US008736830B2

(12) United States Patent
Watanabe et al.

(10) Patent No.: US 8,736,830 B2
(45) Date of Patent: May 27, 2014

(54) PATTERN INSPECTION DEVICE OF SUBSTRATE SURFACE AND PATTERN INSPECTION METHOD OF THE SAME

(75) Inventors: Masahiro Watanabe, Yokohama (JP); Toshihiko Nakata, Hiratsuka (JP); Yasuhiro Yoshitake, Yokohama (JP); Hideaki Sasazawa, Yokohama (JP); Minoru Yoshida, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 449 days.

(21) Appl. No.: 13/145,968

(22) PCT Filed: Dec. 10, 2009

(86) PCT No.: PCT/JP2009/070694
§ 371 (c)(1),
(2), (4) Date: Oct. 5, 2011

(87) PCT Pub. No.: WO2010/098000
PCT Pub. Date: Sep. 2, 2010

(65) Prior Publication Data
US 2012/0013890 A1    Jan. 19, 2012

(30) Foreign Application Priority Data

Feb. 27, 2009    (JP) .................................. 2009-045707

(51) Int. Cl.
*G01N 21/00*    (2006.01)
(52) U.S. Cl.
USPC ..................................... 356/237.1; 356/237.5
(58) Field of Classification Search
USPC ..................... 356/237.1–241.6, 242.1–243.8, 356/426–431, 600–640
See application file for complete search history.

(56) References Cited

U.S. PATENT DOCUMENTS

| 4,330,213 A * | 5/1982 | Kleinknecht et al. .......... 356/496 |
| 6,285,033 B1 * | 9/2001 | Matsumoto ................... 250/548 |
| 2002/0053647 A1 * | 5/2002 | Shiratsuchi et al. ...... 250/559.44 |

FOREIGN PATENT DOCUMENTS

| JP | 2002-350360 A | 12/2002 |
| JP | 2008-082999 | 4/2008 |

* cited by examiner

*Primary Examiner* — Kara E. Geisel
*Assistant Examiner* — Jarreas C Underwood
(74) *Attorney, Agent, or Firm* — McDermott Will & Emery LLP

(57) ABSTRACT

There is provided a pattern inspection device for a substrate surface which can inspect a substrate including a pattern whose size is equal to or smaller than light resolution limit at high speed. The pattern inspection device for the substrate surface includes: a near-field optical head 101 having a fine repetitive pattern; a θ driving unit 311 of scanning an inspected substrate 900 relatively to the near-field optical head 101; a space holding mechanism of holding a space between the near-field optical head 101 and the inspected substrate 900 constant; alight source 110 of irradiating light to the near-field optical head 101; a detection system 201 of detecting an intensity of scattered light generated by interaction between the fine repetitive pattern on the near-field optical head 101 and a fine pattern on a surface of the inspected substrate 900; and a signal processing unit 321 of inspecting the fine pattern on the inspected substrate 900 based on an output of the detection system 201.

13 Claims, 17 Drawing Sheets

TRACK DUTY RATIO = S1 + S2 + S3 + S4

TRACK SHIFT = $\frac{p}{2\pi} \arctan \frac{S1 - S3}{S2 - S4}$

MISSING-PATTERN DETECTION

DUTY DETECTION

- 902 : SERVO PATTERN PORTION
- 101 : NEAR-FIELD OPTICAL HEAD
- 202 : ARRAY DETECTOR
- 903 : BPM PATTERN SURFACE
- TRACK PITCH : p

RADIAL DIRECTION ←

ROTATIONAL DIRECTION (CIRCUMFERENTIAL DIRECTION)

PATTERN INSPECTION DEVICE OF SUBSTRATE SURFACE AND PATTERN INSPECTION METHOD OF THE SAME

RELATED APPLICATIONS

This application is the U.S. National Phase under 35 U.S.C. §371 of International Application No. PCT/JP2009/070694, filed on Dec. 10, 2009, which in turn claims the benefit of Japanese Application No. 2009-045707, filed on Feb. 27, 2009, the disclosures of which Applications are incorporated by reference herein.

TECHNICAL FIELD

The present invention relates to an inspection device for a fine pattern including a pattern whose size is equal to or smaller than a light wavelength, and more particularly, the present invention relates to an inspection technique for a fine pattern whose size is equal to or smaller than a light resolution limit.

BACKGROUND ART

As an inspection technique for a fine shape of a substrate surface, a method of detecting scattered light by irradiating a laser beam has been known. However, in this method, only a foreign substance having a certain size and anomaly such as a missing pattern can be detected.

Also, a method of scanning a sample by an optical microscope with high resolution at a high speed has been known. However, in this method, it is difficult to detect a defect whose size is equal to or smaller than a resolution (0.61λ/NA, λ: light wavelength and NA: numerical aperture (<1) of an objective lens) determined by the light wavelength. Although a fine defect whose size is smaller than 200 nm which is a half of a wavelength of visible light has been handled by, for example, using an expensive deep ultraviolet optical system or others, it is extremely difficult to handle a pattern such as smaller than 100 nm.

More particularly, a defect such as a pattern positional shift is more difficult to appear as image brightness and darkness than a defect such as a lost pattern, an excessive pattern, and adhesion of a foreign substance, and therefore, it is extremely difficult to detect the defect.

Accordingly, conventionally, an inspection method of scanning a substrate by electron beam having high resolution has been known. However, in this method, there are problems that it is difficult to inspect the entire surface of the substrate in realistic time because a scanning speed is too slow, and that normal electron microscopic images cannot be obtained because a substrate having no conductivity such as a quartz substrate is charged due to the use of the electron beam.

Also, Japanese Patent Application Laid-Open Publication No. 2008-82999 (Patent Document 1) discloses an inspection method with fine resolution and without depending on light resolution by detecting the scattered light from a pattern on a substrate when a head approaches the substrate to scan in a state that fine near-field light smaller than light resolution is generated by using a plasmon-enhanced head.

PRIOR ART DOCUMENT

Patent Document

Patent Document 1: Japanese Patent Application Laid-Open Publication No. 2008-82999

DISCLOSURE OF THE INVENTION

Problems to be Solved by the Invention

However, an aim of the method of Patent Document 1 is to inspect a fine asperity defect by the scattered light, and there is a problem that it is difficult to inspect a defect such as fine pattern shift.

Also, an idea such that a plurality of elements generating the near-field light are arranged to increase the speed is disclosed. However, for increasing the speed, it is required to independently detect the scattered light caused by a large number of elements, and therefore, there is a problem that a device is complicated and is not practical.

As described above, in a conventional technique, there is no inspection method at the practical speed for the fine pattern equal to or smaller than the light resolution limit.

Accordingly, a preferred aim of the present invention is to provide a pattern inspection device and a pattern inspection method for a substrate surface, which can inspect a substrate including a pattern equal to or smaller than light resolution limit at high speed.

The above and other preferred aims and novel characteristics of the present invention will be apparent from the description of the present specification and the accompanying drawings.

Means for Solving the Problems

The typical one of the inventions disclosed in the present application will be briefly described as follows.

That is, the typical one includes: a light irradiation mechanism for irradiating light to a head having a fine repetitive pattern or to a substrate surface of an inspection target substrate facing the head; a detector for detecting intensity of scattered light generated by interaction between the fine repetitive pattern on the head and the fine pattern on the surface of the inspection target substrate; and a first signal processing unit for inspecting the fine pattern on the inspection target substrate based on an output of the detector.

Effects of the Invention

The effect obtained by typical aspects of the present invention will be briefly described below.

That is, as the effect obtained by the typical aspects, a substrate including a pattern equal to or smaller than light resolution limit can be inspected at high speed.

BRIEF DESCRIPTIONS OF THE DRAWINGS

BEST MODE FOR CARRYING OUT THE INVENTION

Hereinafter, embodiments of the present invention will be described in detail with reference to the accompanying drawings. Note that components having the same function are denoted by the same reference symbols throughout the drawings for describing the embodiment, and the repetitive description thereof will be omitted.

(First Embodiment)

Figure 1:
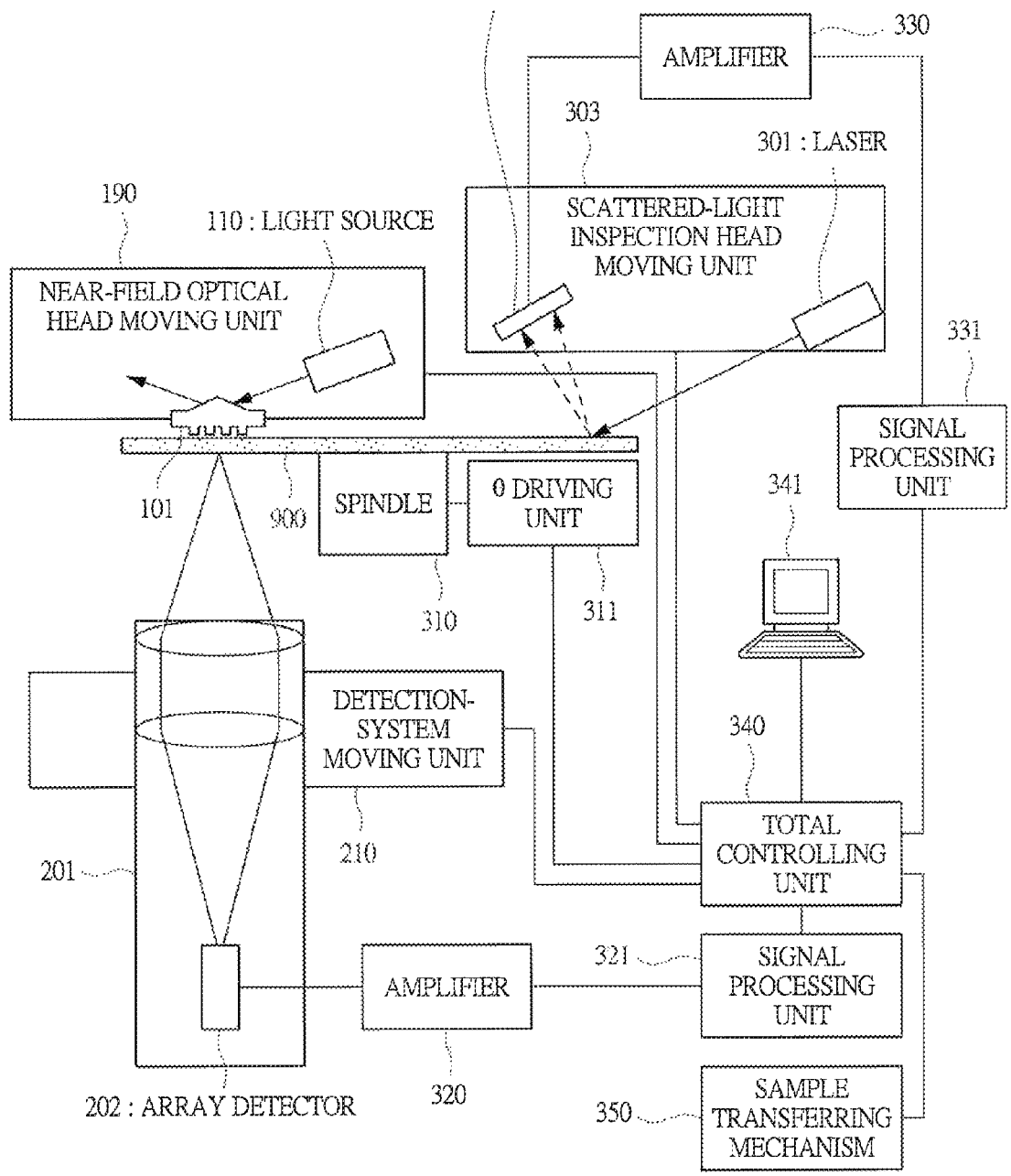
FIG. 1 is a configuration diagram showing a configuration of a pattern inspection device for a substrate surface according to a first embodiment of the present invention.

With reference to FIG. 1, a configuration of a pattern inspection device for a substrate surface according to a first embodiment of the present invention is described. FIG. 1 is a configuration diagram showing the configuration of the pattern inspection device for the substrate surface according to the first embodiment of the present invention.

In FIG. 1, the pattern inspection device for the substrate surface includes: a near-field optical head 101 having a fine repetitive pattern; a light source 110; a near-field optical head moving unit 190; a detection system 201; an array detector 202; a detection-system moving unit 210; a scattered-light inspection light source (laser) 301; a scattered-light detector 302; a scattered-light inspection head moving unit 303; a spindle 310; a θ driving unit 311; an amplifier 320; a signal processing unit 321; an amplifier 330; a signal processing unit 331; a total controlling device 340; a user interface 341; and a sample transferring mechanism 350.

The near-field optical head 101 is irradiated by light rays from the light source 110 which is a light irradiation mechanism. The light scattered by an inspected substrate 900 which is an inspection target substrate facing the near-field optical head 101 so as to interpose a space equal to or smaller than a wavelength of the illumination light is substantially imaged on the array detector 202 by the detection system 201.

As holding the space between the near-field optical head 101 and the inspected substrate 900 by a space holding mechanism, they are relatively moved in a horizontal direction to the space by a driving mechanism, so that the pattern on the inspected substrate 900 can be inspected.

As one method of achieving the relative movement by the driving mechanism, the inspected substrate 900 may be rotated by rotation of the spindle 310 on which the inspected substrate 900 is loaded, the near-field optical head 101 may be substantially moved in a radial direction of the spindle 310 by the near-field optical head moving unit 190, and the detection system 201 may be moved in synchronization with the movement of the near-field optical head 101 by the detection-system moving unit 210.

At this time, the detection-system moving unit 210 and the near-field optical head moving unit 190 may be integrally driven by the same actuator. The spindle 310 is driven by the total controlling device 340 through the θ driving unit 311. Also, the near-field optical head moving unit 190 and the detection-system moving unit 210 are also controlled by the total controlling device 340. In this manner, the relative movement of the near-field optical head 101 to the inspected substrate 900 can be achieved.

An intensity signal of the scattered light detected by the array detector 202 is enhanced by the amplifier 320, and then, is processed by the signal processing unit 321 to obtain defect information. This process will be described in detail later.

In addition, it includes an optical system of detecting a defect such as a foreign substance and a scratch on the inspected substrate 900 by irradiating light from a high-intensity light source such as the laser 301 to the inspected substrate 900 and detecting the scattered light due to the irradiation by the scattered-light detector 302.

This optical system scans over the inspected substrate 900 as moved by the scattered-light inspection head moving unit 303 through the total controlling device 340, a signal obtained at this time from the scattered-light detector 302 is amplified by the amplifier 330, and this signal is processed by the signal processing unit 331, so that the defect such as a relatively large foreign substance and scratch on the inspected substrate 900 can be detected.

In this manner, although there is a possibility that the scratch or the foreign substance on the inspected substrate 900 hits the near-field optical head 101 to damage the inspected substrate 900 or the near-field optical head 101 in the inspection for a narrow gap by the near-field optical head 101, the damage can be prevented by previously detecting such a scratch and a defect.

Also, the total controlling device 340 achieves functions of controlling the sample transferring mechanism 350 to eject the inspected substrate 900 from a sample cassette (not shown), transfer it, and automatically load it on the spindle 310, and, after the completion of inspection, eject the inspected substrate 900 from the spindle 310, and store it into the sample cassette (not shown). Further, via the user interface 341, the total controlling device 340 also achieves functions of inputting an inspection condition and displaying the inspection result.

Figure 2A:
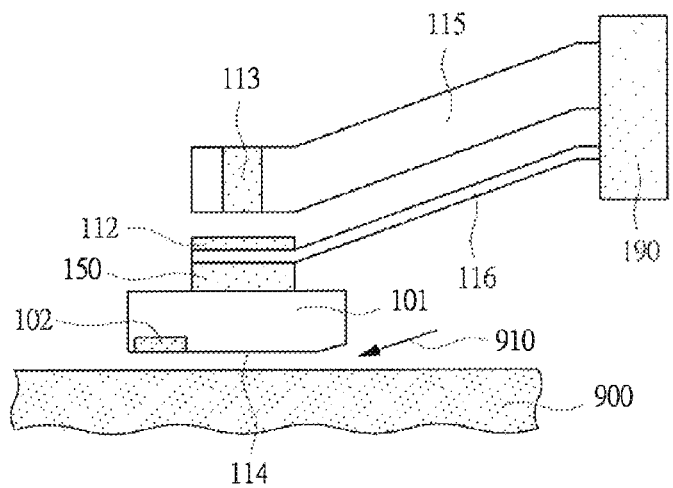
FIGS. 2A to 2C are explanatory diagrams each explaining a method of holding a space between an inspected substrate and a near-field optical head in the pattern inspection device for the substrate surface according to the first embodiment of the present invention.
Figure 2B:
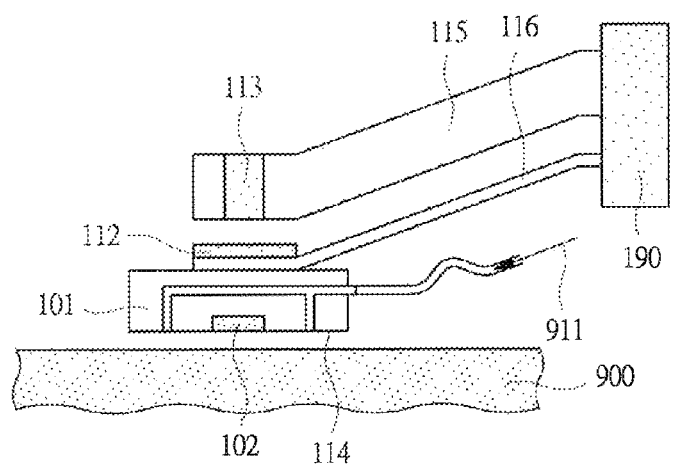
Figure 2C:
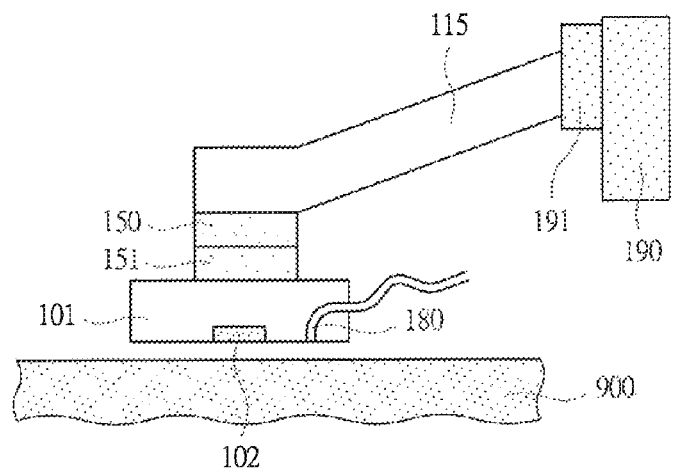

Here, with reference to FIGS. 2A to 2C, a method of holding a space between an inspected substrate and a near-field optical head in the pattern inspection device for the substrate surface according to the first embodiment of the present invention is described. FIGS. 2A to 2C are explanatory diagrams each explaining the method of holding the space between the inspected substrate and the near-field optical head in the pattern inspection device for the substrate surface according to the first embodiment of the present invention.

In FIG. 2A, a dynamic pressure floating system normally used for floating a head of a hard disk is applied. An elastic support body 116 is extended from a movable part of the near-field optical head moving unit 190, and the near-field optical head 101 is attached to a tip of the elastic support body. When a positional accuracy in the radial direction of the inspected substrate 900 is not sufficient by using only the near-field optical head moving unit, a tracking actuator 150 is inserted between the elastic support body 116 and the near-field optical head 101.

This tracking actuator is constituted of a piezo element or others, and can finely drive the near-field optical head in the radial direction of the inspected substrate 900. When the inspected substrate 900 is rotated, an air layer 910 is generated between the inspected substrate 900 and a floating surface 114 formed on a lower surface of the near-field optical head 101 to generate an upward force, and the near-field optical head is stably floated at a point where this force balances a pushing force of the elastic support body 116 as holding a fine space equal to or smaller than the light wavelength.

Further, another beam 115 is extended from the movable part of the near-field optical head moving unit 190, and a coil 113 is attached to a tip of the beam. A magnetic plate 112 is attached to a tip of the elastic support body 116 to lift the near-field optical head 101 by applying a current to the coil 113. By using this function, the near-field optical head 101 is temporarily lifted at a position where the defect such as the large foreign substance and scratch is detected by the scattered-light detector 302 so as to protect the near-field optical head 101 and the inspected substrate 900.

Still further, this coil 113 is used also for evacuating the near-field optical head 101 when the inspected substrate 900 is loaded and unloaded by the sample transferring mechanism 350 before and after the inspection.

In FIG. 2B, as another example, instead of the dynamic pressure floatation with using the movement of the inspected surface 900, static pressure floatation is achieved by blowing a floating air 911 to the floating surface 114.

Figure 18:
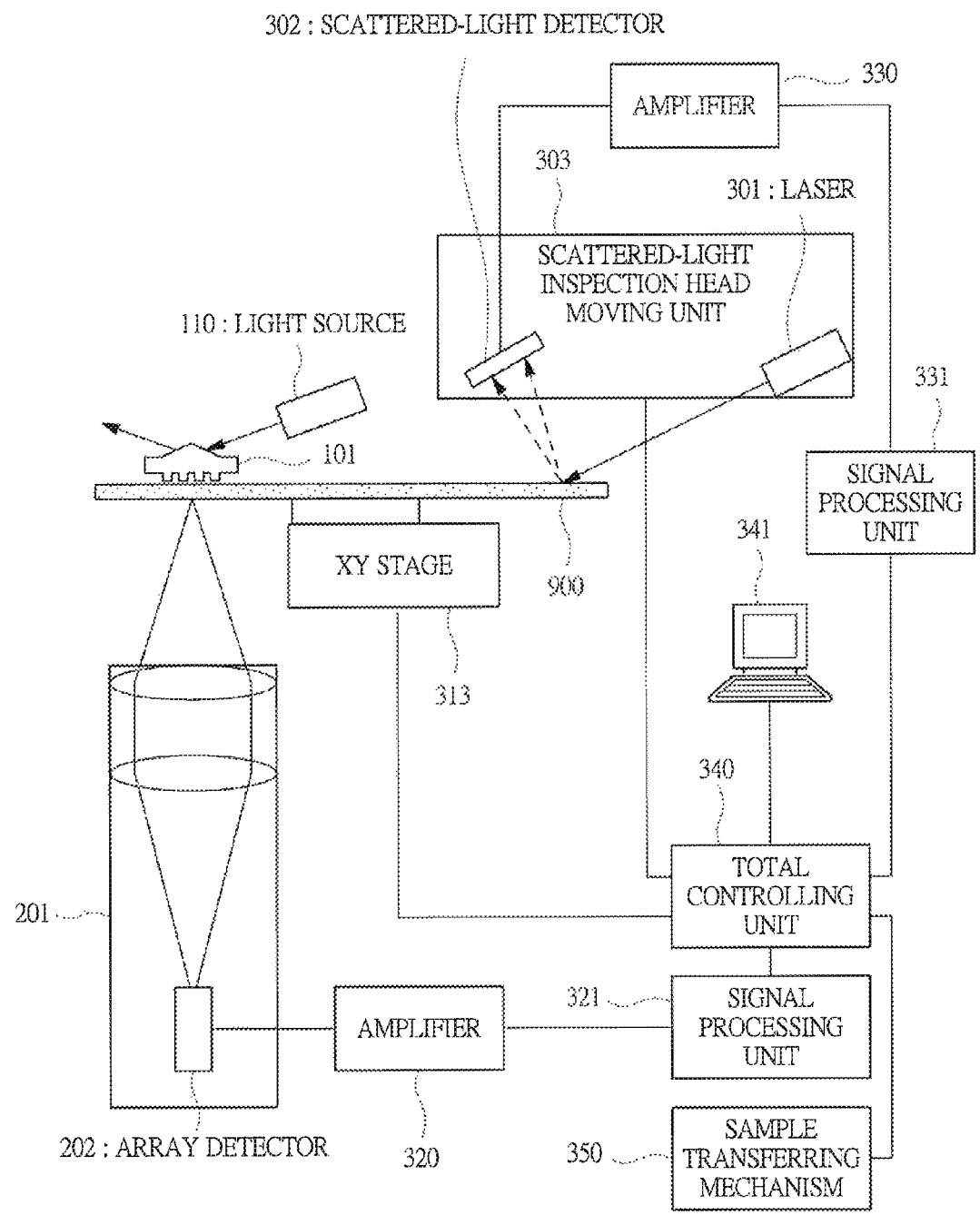
FIG. 18 is a configuration diagram showing a configuration with an XY stage of the pattern inspection device for the substrate surface according to the fifth embodiment of the present invention.

In this manner, the stable space can be held even when a speed at which the inspected substrate 900 is rotated is slow or even when a relative speed of the inspected substrate 900 to the near-field optical head 101 varies as when the inspected substrate 900 is driven back and forth and right and left by an XY stage 313 as shown in FIG. 18 described later. Although not shown, even in this case, it goes without saying that the actuator 150 may be inserted between the elastic support body 116 and the near-field optical head 101.

As still another example, FIG. 2C shows a method of actively controlling the space. A near-field optical head up/down mechanism 191 is fixed to the movable part of the near-field optical head moving unit 190. The beam 115 is extended from the mechanism, and the near-field optical head 101 is attached to the tip of the beam 115 through the tracking actuator 150 and a space controlling actuator 151.

The tracking actuator 150 is composed of a piezo element or others, and can finely drive the near-field optical head in the radial direction of the inspected substrate 900. The space controlling actuator 151 drives the near-field optical head 101 upward and downward. In order to control the space, a space measuring device 180 is embedded into the near-field optical head 101.

The space between the near-field optical head 101 and the inspected substrate 900 measured by the space measuring device 180 is fed back to the space controlling actuator 151 so as to hold a constant space. The near-field optical head up/down moving mechanism 191 temporarily lifts the near-field optical head 101 at the position where the defect such as the large foreign substance and scratch is detected by the scattered-light detector 302 to protect the near-field optical head 101 and the inspected substrate 900.

Also, this coil 113 is used also for the evacuation when the inspected substrate 900 is loaded and unloaded by the sample transferring mechanism 350 before and after the inspection. Alternatively, when the near-field optical head 101 is temporarily lifted at the position where the defect such as the foreign substance and scratch is detected, the space controlling actuator 151 with quicker response may be used.

Figure 3A:
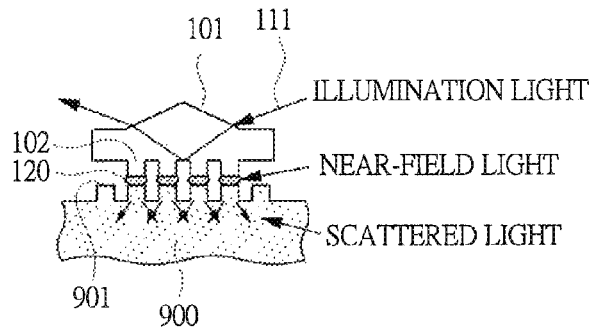
FIGS. 3A to 3C are explanatory diagrams each explaining a relationship between a pattern on the inspected substrate and the near-field optical head in the pattern inspection device for the substrate surface, and a method of detecting a fine defect equal to or smaller than light resolution according to the first embodiment of the present invention.
Figure 3B:
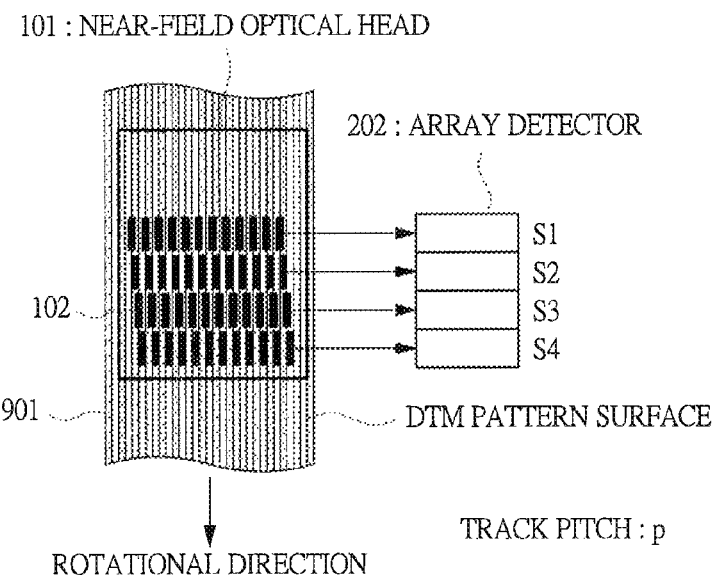
Figure 3C:
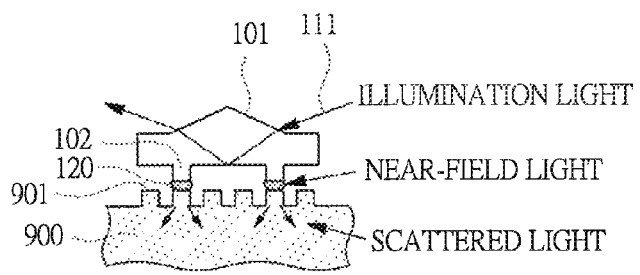

Next, with reference to FIGS. 3A to 3C, a relationship between a pattern on the inspected substrate and the near-field optical head in the pattern inspection device for the substrate surface, and a method of detecting a fine defect equal to or smaller than light resolution according to the first embodiment of the present invention are described. FIGS. 3A to 3C are explanatory diagrams each explaining a relationship between a pattern on the inspected substrate and the near-field optical head in the pattern inspection device for the substrate surface, and a method of detecting a fine defect equal to or smaller than light resolution according to the first embodiment of the present invention.

FIG. 3A is a cross-sectional view of an on-substrate pattern 901 and the near-field optical head 101. The near-field optical head 101 is composed of a material which transmits a wavelength of illumination light 111, and a fine periodic near-field light generating pattern 102 is formed on the near-field optical head 101.

When the illumination light 111 is irradiated to this at a low angle, the illumination light is totally reflected on a surface of the near-field optical head 101. Although the light as propagation light does not transmit the inspected substrate 900 side, a periodic near-field light 120 is generated in a periphery of the periodic near-field light generating pattern 102.

When upper and lower surfaces of the near-field optical head 101 are parallel to each other, a condition of the total reflection is not satisfied even if the illumination light 111 enters thereto at any angle. However, as shown in FIG. 3A, by inclining an incident part of the illumination light 111 on a rear surface of the near-field optical head 101, the condition of the total reflection of the illumination light 111 on the lower surface of the near-field optical head 101 can be created.

The near-field light 120 does not propagate in this state. However, when the on-substrate pattern 901 on the inspected substrate 900 is approached, the near-field light 120 is scattered by this pattern, and the scattered light is propagated. By forming the periodic near-field light generating pattern 102 so as to have the same period as that of the on-substrate pattern 901, the scattered light is enhanced when phases of both patterns are matched with each other as shown in FIG. 3A.

Generally, the near-field light is weak. However, there is an effect that, by simultaneously detecting the scattered light from such a plurality of patterns, a detected light intensity can be increased.

Also, in an inspection method by point-shaped near-field light, there is a problem that a scan distance, that is, inspection time required for the entire inspection for the inspected substrate 900 is increased in inverse proportion to a magnitude of the near-field light, that is, the detection resolution. However, as described in the present embodiment, by using the periodic near-field pattern over a wide area, the scan distance, that is, the inspection time required for the entire inspection for the inspected substrate 900 can be shortened as maintaining the detection resolution.

FIG. 3B is a diagram in which this near-field optical head is viewed from above. It is assumed that a pattern is periodically arranged as the on-substrate pattern 901 on the inspected substrate 900 which is an inspection target. For example, in a discrete-track media which has been developed as a storage medium of a next-generation hard disk, a magnetic pattern is circumferentially arranged, and information can be recorded by running a recording/reading head on each pattern (called track).

Four types of regions having such a plurality of periodic near-field light generating patterns 102 whose phases are shifted by 90 degrees from each other are provided on the near-field optical head 101. The scattered light is substantially imaged on the array detector 202 by the optical system of the detection system 201, and pieces of intensity information S1, S2, S3, and S4 of the scattered light from respective regions are independently detected.

In the array detector 202, it is desirable to arrange an optical detector which can detect the weak light in an array. For example, a combination of an avalanche photodiode array, a photomultiplier (photomultiplier tube) array, a micro channel plate, and a photodiode array is desirable.

By such a configuration, a positional shift of the track and a width thereof can be calculated from the S1, S2, S3, and S4.

When a relationship between a scattering intensity and the phase between the near-field optical head 101 and the on-substrate pattern 901 shows a sinusoidal shape, with using a ratio of "S1-S3" to "S2-S4", the track shift can be detected as "(track pitch/$2\pi$) arctan (S1-S3)/(S2-S4)".

Also, a duty ratio of the track can be assumed from "S1+S2+S3+S4". The relationship between the phase and the scattering intensity practically is shifted from an exact sinusoidal wave. However, by previously obtaining a relationship between the phase and the S1, S2, S3, and S4 or between the phase and (S1-S3)/(S2-S4) when the phase shift occurs from an experiment or an optical simulation, the phase can be obtained from the S1, S2, S3, and S4 with using this relationship.

Further, by similarly obtaining a relationship between the duty ratio of the track and the S1, S2, S3, and S4 or between the duty ratio of the track and the "S1+S2+S3+S4" from an experiment or an optical simulation, the duty ratio of the track can be obtained from the S1, S2, S3, and S4 with using this relationship. These calculations are performed by the signal processing unit 321.

Note that, in the present embodiment, the scattered light is detected by making a difference of a positional-shift amount to the four regions. However, since the sinusoidal-wave signal whose pitch is determined is expressed by three parameters of amplitude, phase, and offset, at least signals of three types of the positional-shift amounts may be detected. Also, more particularly, in order to increase an accuracy when the signal shape is shifted from the sinusoidal wave, for example, six types of signals whose phases are shifted by 60 degrees from each other may be detected, or eight types of signals whose phases are shifted by 45 degrees from each other may be detected.

Further, since the regions S1, S2, S3, and S4 are arranged back and forth, the signals are time shifted, and the shifted time is obtained by dividing a space between the regions by a scan speed. Therefore, the shifted time is corrected by the signal processing unit 321 before the above-described calculation to adjust the time, and then, the calculation is performed.

The scan speed obtained when the inspected substrate 900 is rotationally driven by the spindle 310 is expressed as multiplication of a rotational angular velocity by a radius, and therefore, the shifted time is different depending on a scanned position on the radius.

Note that, as shown in FIG. 3C, a pitch of the periodic near-field light generating pattern 102 may be not equal to a pitch of the on-substrate pattern 901 but the integral multiple of that of the on-substrate pattern 901. FIG. 3C shows an example that the pitch of the periodic near-field light generating pattern 102 is three times the pitch of the on-substrate pattern 901. Also in this case, as long as a size (width) of each pattern of the periodic near-field light generating pattern 102 is the same as that of the on-substrate pattern 901, the signals S1, S2, S3, and S4 show the sinusoidal-wave-shaped response with respect to a phase based on the pitch of the on-substrate pattern 901, and therefore, the same result can be obtained by the same processing as that of the case shown in FIG. 3A.

Figure 4:
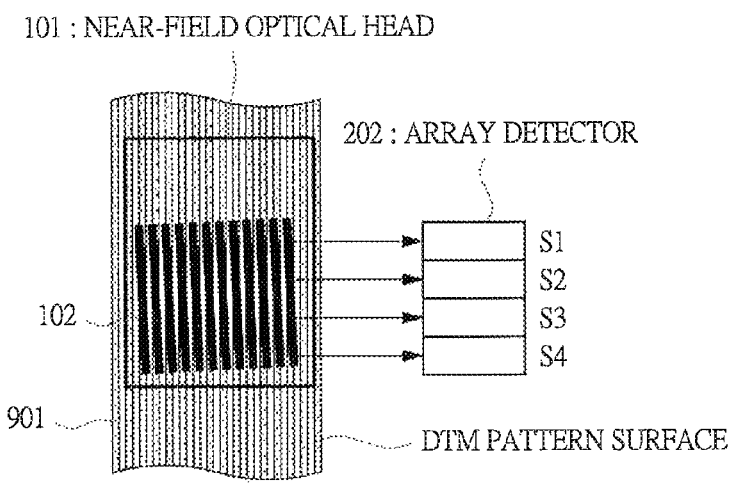
FIG. 4 is an explanatory diagram explaining arrangement of the near-field optical head of the pattern inspection device for the substrate surface according to the first embodiment of the present invention.

Also, the near-field optical head can be arranged also as shown in FIG. 4. FIG. 4 is an explanatory diagram explaining the arrangement of the near-field optical head of the pattern inspection device for the substrate surface according to the first embodiment of the present invention.

As shown in FIG. 4, the periodic near-field light generating pattern 102 is arranged to be inclined and opposed to the on-substrate pattern 901. Accordingly, in accordance with a position in upward and downward direction in FIG. 4 on the periodic near-field light generating pattern 102, the phase of the periodic near-field light generating pattern 102 with respect to the on-substrate pattern 901 is changed.

The periodic near-field light generating pattern 102 is imaged on three or more regions, for example, four regions of the array detector 202 by the detection system 201, and the scattering intensity is detected for each region. At this time, by setting an inclined degree of the periodic near-field light generating pattern 102 so that an average phase shift of each region is shifted by 90 degrees from each other, the same result as that of FIG. 3B can be obtained.

Note that, in FIG. 4, the periodic near-field light generating pattern 102 is inclined with respect to the near-field optical head 101. However, it goes without saying that the near-field optical head 101 and the periodic near-field light generating pattern 102 are formed in parallel to each other, and the near-field optical head 101 is inclined when the near-field optical head 101 is held with the inspected substrate 900 of the inspection target.

Figure 5:
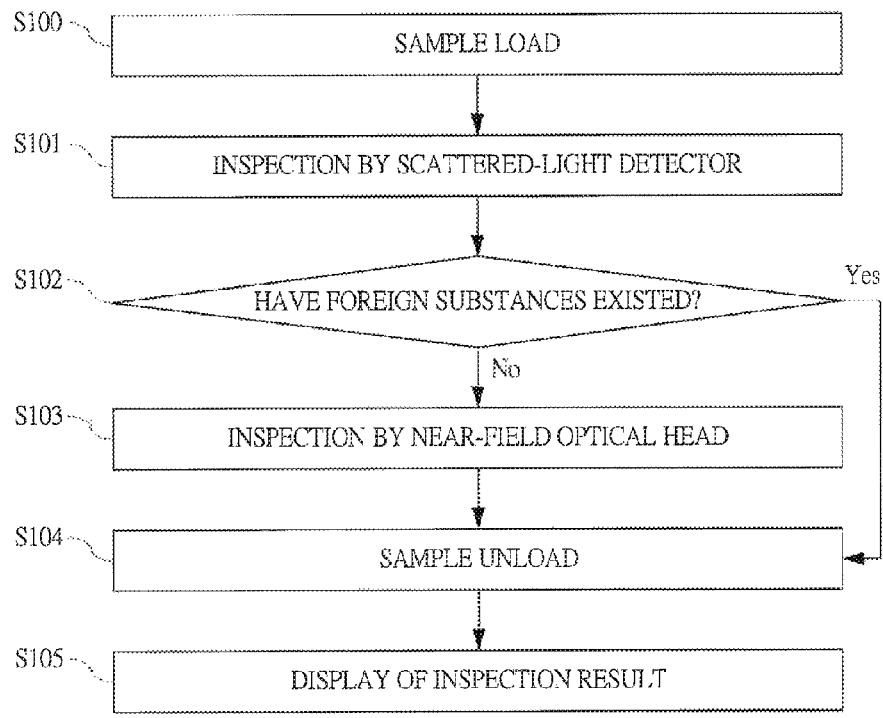
FIG. 5 is a flowchart showing an inspection procedure for the inspected substrate in the pattern inspection device for the substrate surface according to the first embodiment of the present invention.
Figure 6:
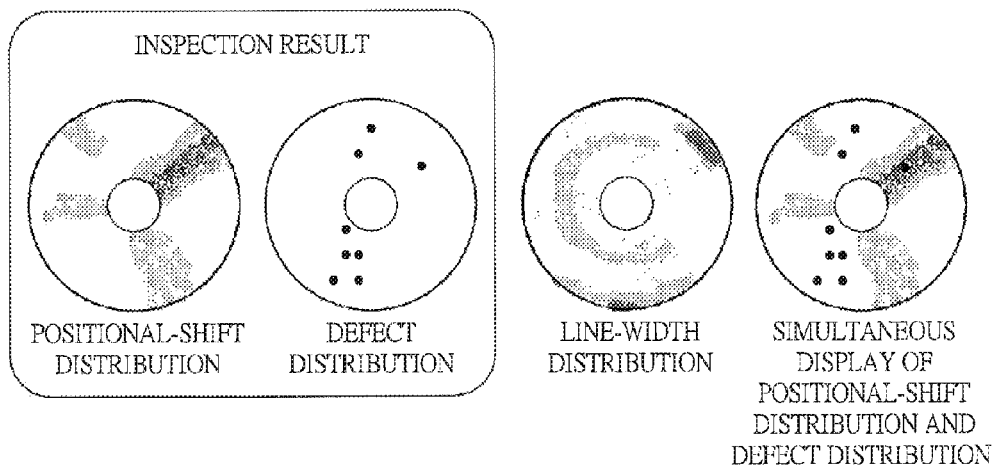
FIG. 6 is a diagram showing one example of an inspection result of the pattern inspection device for the substrate surface according to the first embodiment of the present invention.

Next, with reference to FIGS. 5 and 6, an inspection procedure for the inspected substrate in the pattern inspection device for the substrate surface according to the first embodiment of the present invention and an inspection result thereof are described. FIG. 5 is a flowchart showing the inspection procedure for the inspected substrate in the pattern inspection device for the substrate surface according to the first embodiment of the present invention, and FIG. 6 is a diagram showing one example of the inspection result of the pattern inspection device for the substrate surface according to the first embodiment of the present invention.

First, the total controlling device 340 controls the sample transferring mechanism 350 to load a sample from a cassette (S100). Next, the foreign substance is detected by the scattering-light detector 302 (S101), and it is determined whether there is the large foreign substance or not from a detection result of the foreign substance by the scattering-light detector 302 at S101 (S102).

When it is determined that there is the large foreign substance at S102, the inspection by the near-field optical head 101 is skipped, and the inspected substrate 900 is unloaded (S104).

When it is determined that there is no large foreign substance at S102, the inspection is performed by the near-field optical head 101 (S103), the inspected substrate 900 is unloaded (S104), and an inspection result is displayed (S105).

This inspection result is displayed such that a distribution of the positional-shift amount or the line width on the inspected substrate 900 is shown by shading as shown in FIG. 6. Also, a defect detection point can be shown by a dot on a map, and besides, the distribution of the positional shift and the defect distribution can be simultaneously shown on the same map.

Note that, when there is the large foreign substance at S102, instead of skipping the inspection by the near-field optical head 101, an inspection only for a point where there is the large foreign substance or for a circumference including the point where there is the large foreign substance may be skipped.

Further, instead of sequentially performing the inspection by the scattering-light detector 302 and the inspection by the near-field optical head 101, as parallely performing both in order to increase the inspection speed, the inspection by the scattering-light detector may be performed slightly prior to that by the near-field optical head 101.

In this case, this operation can be performed by providing the scattered-light inspection head moving unit 303 separately from the near-field optical head moving unit 190 and the detection-system moving unit 210 as shown in FIG. 1, and controlling an inspection portion by the scattered light independently to an inspection portion by the near-field light.

Figure 17:
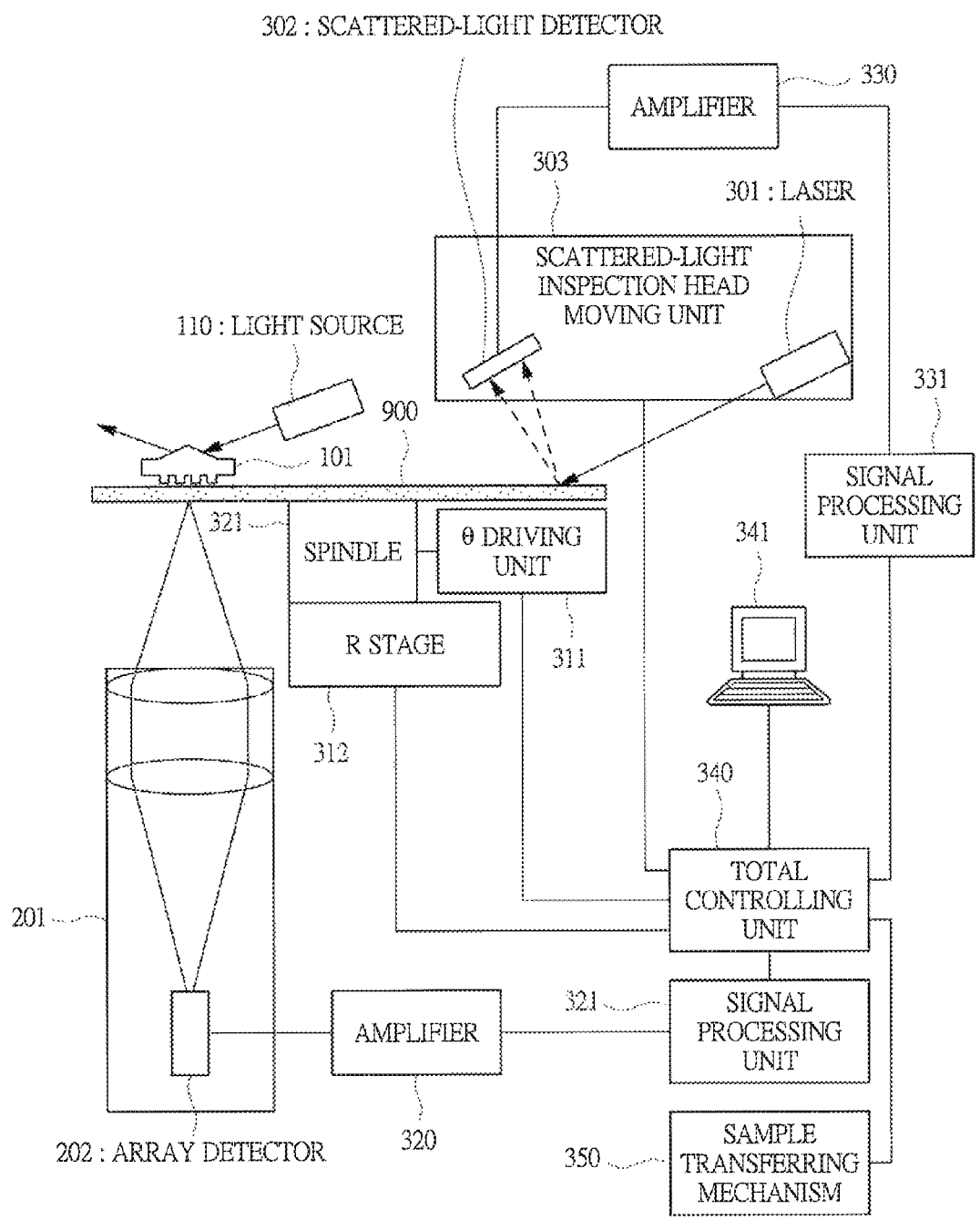
FIG. 17 is a configuration diagram showing a configuration with an R stage of a pattern inspection device for a substrate surface according to a fifth embodiment of the present invention.

Alternately, this operation can be performed by providing the scattered-light inspection head moving unit 303 separately from an R stage 312 as shown in FIG. 17 described later, and controlling the inspection portion by the scattered light independently to the inspection portion by the near-field light.

Alternately, this operation can be performed by providing the scattered-light inspection head moving unit 303 separately from an XY stage 313 as shown in FIG. 18 described later, and controlling the inspection portion by the scattered light independently to the inspection portion by the near-field light.

Conversely, in the case of sequentially performing the inspection by the scattering-light detector 302 and the inspection by the near-field optical head 101, the scattered-light inspection head moving unit 303 as shown in FIG. 17 or 18 described later is not necessarily required.

As described above, in the present embodiment, the near-field optical head 101 which generates the near-field light pattern scans at a high speed as being close to the inspected substrate 900, and the scattered light by the interaction between the pattern on the inspected substrate 900 and the near-field light pattern generated by the near-field optical head 101 is detected, so that the pattern on the inspected substrate 900, which is equal to or smaller than the light resolution limit, can be detected.

Further, the pitch of the near-field light pattern is set to be equal to the pitch of the inspected pattern of the inspected substrate 900 or set to be the integral multiple of the pitch thereof, the plurality of the patterns are provided so that their phases are shifted from each other, and their intensities are compared with each other, so that the positional shift of the fine pattern can be inspected, and the defect such as the missing pattern and the pattern size anomaly can be inspected by the entire intensity increase/decrease.

Further, the scattered light from the plurality of patterns are collectively detected, so that a problem of S/N reduction due to the high speed detection can be handled.

Still further, the laser beam collected from the laser 301 is irradiated to the inspected substrate 900, and the scattered light caused by the irradiation is detected, so that a relatively large foreign substance can be detected, and besides, the inspection can be stopped so as not to damage either the near-field optical head 101 or the inspected substrate 900 due to the insertion of the foreign substance into the space between the near-field optical head 101 and the inspected substrate 900, the space being required to be held as the narrow gap, or the inspection can be performed as skipping the foreign substance detection point.

(Second Embodiment)

In a second embodiment, instead of the near-field optical head 101 in the first embodiment, a head using plasmon phenomenon is used.

The configuration and the operation of the pattern inspection device for the substrate surface of the present embodiment is the same as those of the first embodiment.

Figure 7A:
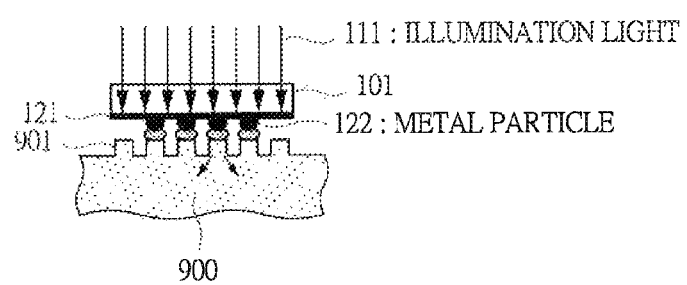
FIGS. 7A and 7B are configuration diagrams each explaining a configuration of a near-field optical head of a pattern inspection device for a substrate surface according to a second embodiment of the present invention.
Figure 7B:
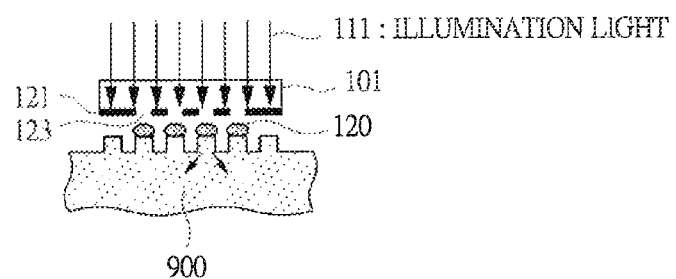
Figure 8A:
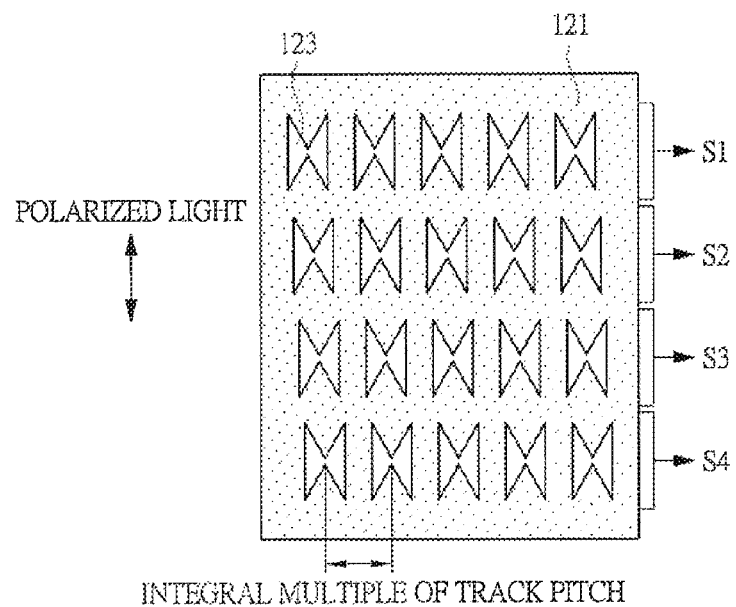
FIGS. 8A and 8B are configuration diagrams each explaining a configuration of a metal film of the near-field optical head of the pattern inspection device for the substrate surface according to the second embodiment of the present invention.
Figure 8B:
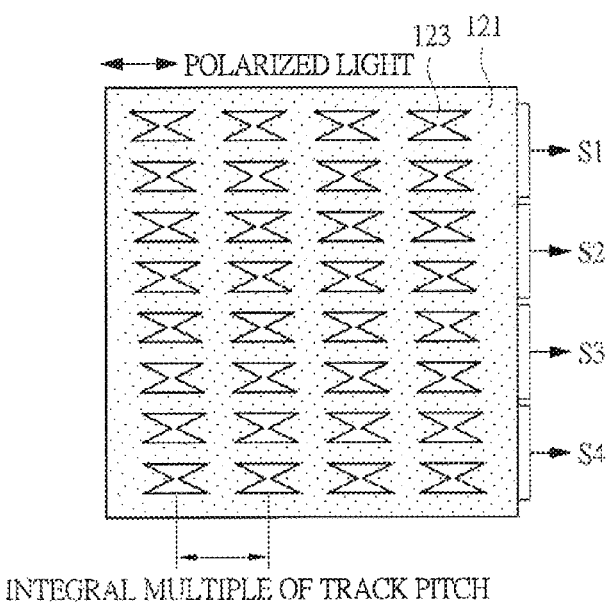

With reference to FIGS. 7A to 8B, a configuration of the near-field optical head of the pattern inspection device for the substrate surface according to the second embodiment of the present invention is described. FIGS. 7A and 7B are configuration diagrams each explaining the configuration of the near-field optical head of the pattern inspection device for the substrate surface according to the second embodiment of the present invention, and FIGS. 8A and 8B are configuration diagrams each explaining a configuration of a metal film of the near-field optical head of the pattern inspection device for the substrate surface according to the second embodiment of the present invention.

As shown in FIG. 7A, on a metal film 121 on a surface of the near-field optical head 101, metal particles 122 are arranged to be aligned.

The metal particles 122 are aligned to have a pitch as large as or integral multiple of that of an on-substrate pattern 901 of an inspected substrate 900 which is an inspection target. When the illumination light 111 is irradiated to the metal particles, the metal particles 122 are localized, and the plasmon which is the collective oscillation state of free electrons in the metal particles is excited.

When the on-substrate pattern 901 approaches the metal particles 122 in the plasmon exciting state, the scattered light is generated on the on-substrate pattern 901, and therefore, the near-field optical head 101 functions as a periodic near-field light generating head similarly to the example shown in FIG. 3 in the first embodiment.

Since the resonance excitation by the plasmon is used, there is an advantage that the detection light with a stronger intensity can be obtained.

FIG. 7B shows a configuration example of still another near-field optical head 101 using the plasmon. As shown in FIG. 7B, a nano gap is formed in the metal film 121, and the illumination light 111 is irradiated to the nano gap, so that the plasmon is generated.

When this state is viewed from a direction vertical to the metal film, the state is as shown in FIGS. 8A and 8B. As shown in FIGS. 8A and 8B, in the metal film, a pattern gap as outlined is provided. The gap is formed so that sharp portions in the metal film are faced to each other. When the light polarized in the direction shown in FIGS. 8A and 8B is irradiated to the gap, plasmon having high intensity is generated on a portion of the metal film facing gap.

By forming a pitch in a lateral direction of the nano gap of the metal film to be as large as or integral multiple of the pitch of the on-substrate pattern 901, the scattered light similarly to that of the first embodiment can be generated.

Further, in a longitudinal direction, a pitch whose position is shifted by ¼ period of the on-substrate pattern 901 is arranged, and the scattered light from each region is detected by each of elements S1 to S4 of the array detector.

FIG. 8A shows the case that the polarized light is in the vertical direction to the diagram, and FIG. 8B shows the case that the polarized light is in the lateral direction to the diagram. Note that a basic configuration in the present embodiment is the arrangement of the plasmon-enhanced pattern, and it goes without saying that the derived type shape may be used as long as each shape of the plasmon-enhanced pattern is a shape having the same plasmon-enhanced effect.

(Third Embodiment)

In a third embodiment, other defects other than the positional shift in the first embodiment are detected.

The configuration and the operation of the pattern inspection device for the substrate surface of the present embodiment are the same as those of the first embodiment.

Figure 9A:
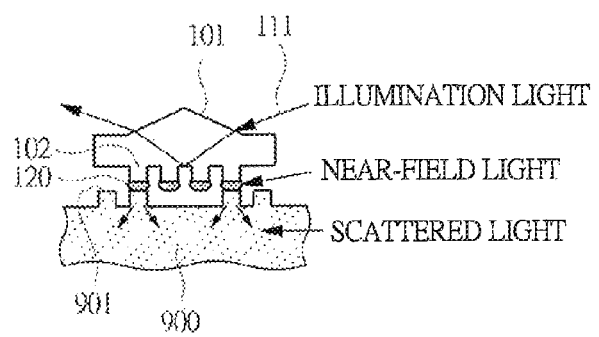
FIGS. 9A and 9B are explanatory diagrams each explaining an inspection method of detecting a missing pattern and pattern width anomaly in a pattern inspection device for a substrate surface according to a third embodiment of the present invention.
Figure 9B:
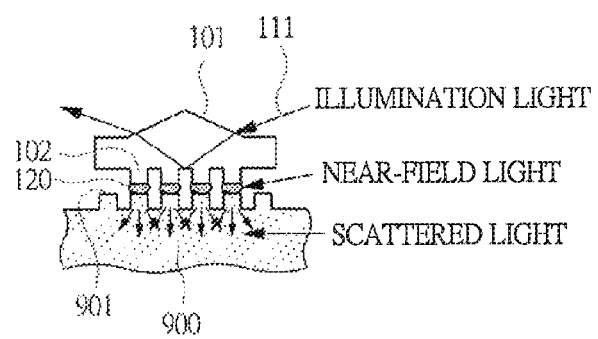
Figure 10:
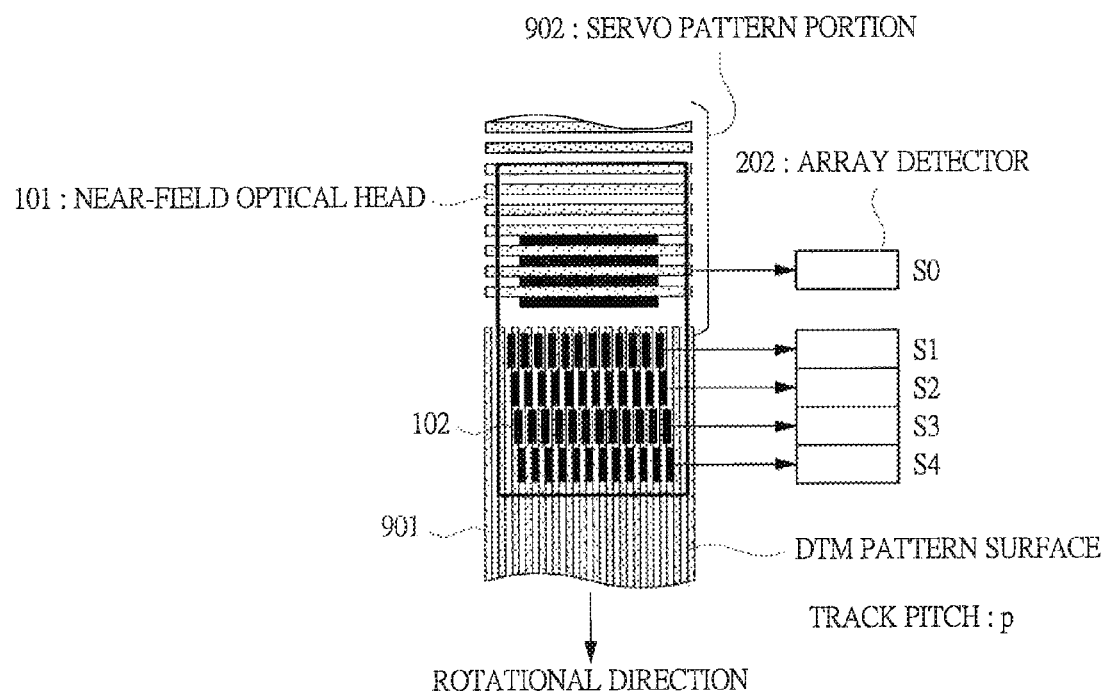
FIG. 10 is an explanatory diagram explaining an inspection method with including a servo pattern portion of a discrete-track media substrate in the pattern inspection device for the substrate surface according to the third embodiment of the present invention.
Figure 11A:
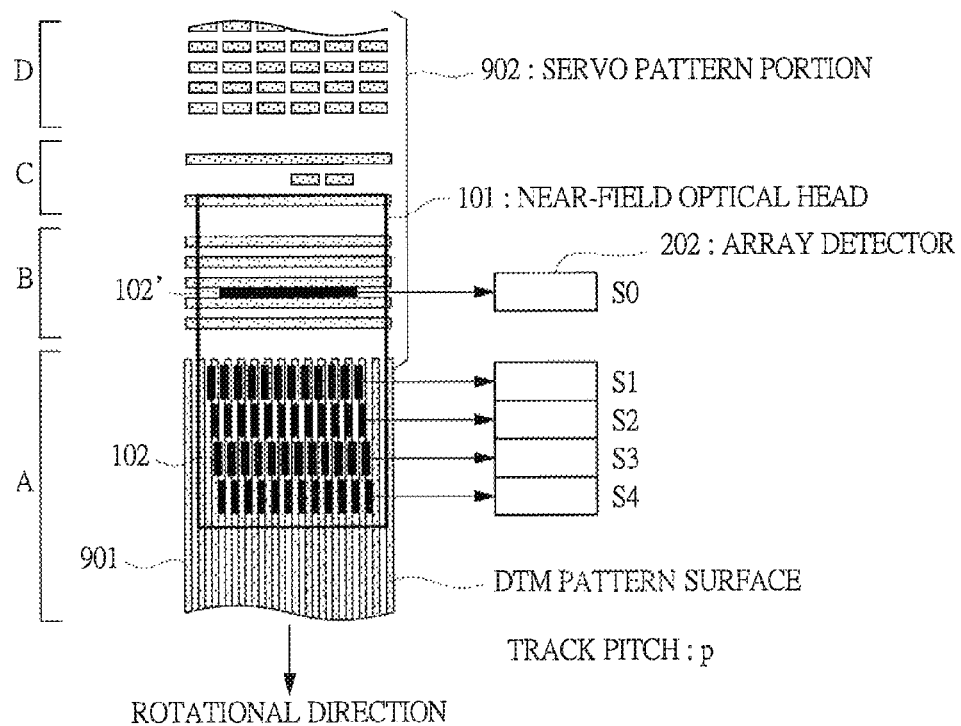
FIGS. 11A and 11B are explanatory diagrams each explaining an inspection method with including another servo pattern portion of the discrete-track media substrate in the pattern inspection device for the substrate surface according to the third embodiment of the present invention.
Figure 11B:
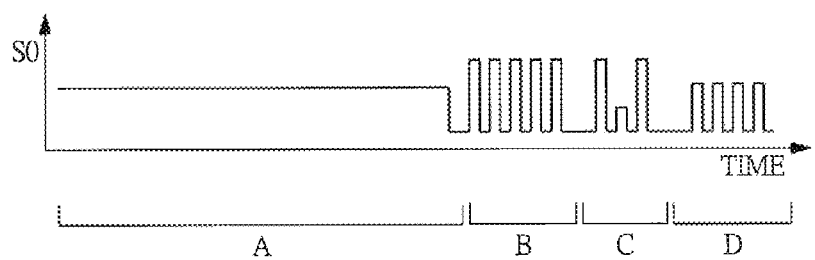
Figure 12:
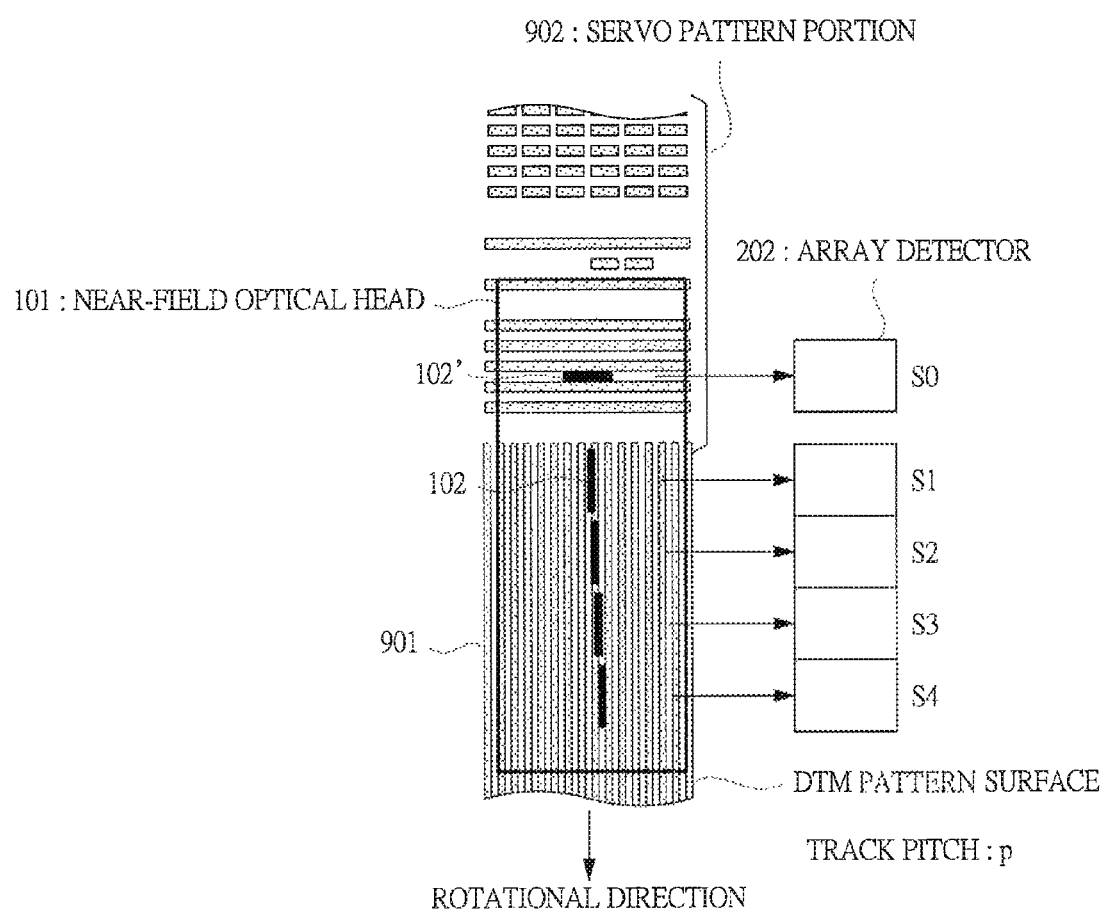
FIG. 12 is an explanatory diagram explaining an inspection method with including still another servo pattern portion of a discrete-track media substrate in the pattern inspection device for the substrate surface according to the third embodiment of the present invention.
Figure 13A:
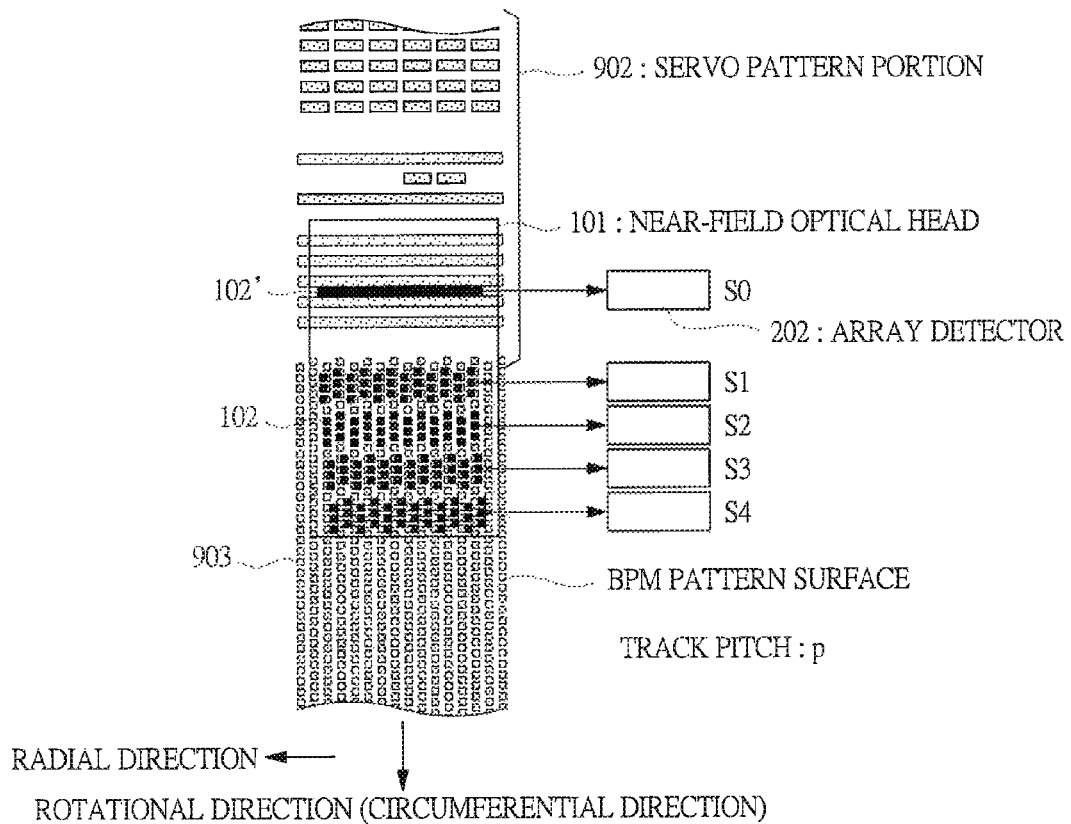
FIGS. 13A to 13C are explanatory diagrams each explaining an inspection method with including a servo pattern portion of a bit-patterned media substrate in the pattern inspection device for the substrate surface according to the third embodiment of the present invention.
Figure 13B:
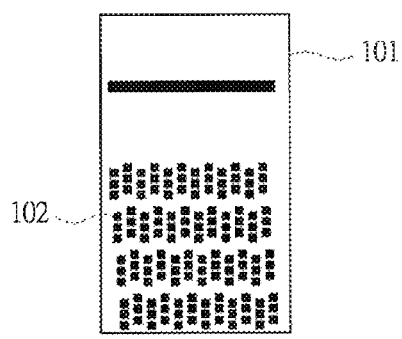
Figure 13C:
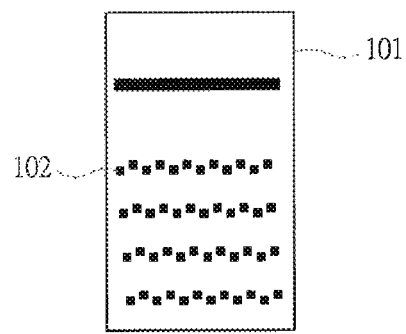

With reference to FIGS. 9A to 13C, an inspection method of a pattern inspection device for a substrate surface according to a third embodiment of the present invention is described. FIGS. 9A to 13C are explanatory diagrams each explaining the inspection method of the pattern inspection device for the substrate surface according to the third embodiment of the present invention, FIGS. 9A and 9B show a method of detecting the missing pattern and the pattern width anomaly, FIGS. 10 to 12 show an inspection method with including a servo pattern portion of a discrete-track media substrate, and FIGS. 13A to 13C show an inspection method with including a servo pattern portion of a bit-patterned media substrate.

First, in the detection of the pattern missing or the anomaly of the pattern width, when the on-substrate pattern 901 has a missing portion as shown in FIG. 9A, the scattered light is weak in the missing portion, and therefore, a total intensity of the scattered light is reduced by this weakness.

Also, when the on-substrate pattern 901 is wide (has a high duty ratio) as shown in FIG. 9B, a coupling efficiency between the near-field light 120 and the on-substrate pattern 901 is changed, and therefore, the total intensity of the scatter light is changed. By using this phenomenon, the missing pattern or the pattern-width change can be detected.

Note that, even when the plasmon-enhanced effect as shown in FIGS. 7A and 7B is used, they can be similarly detected.

Here, when it is desired to distinguish FIG. 9A from FIG. 9B, signal time change may be used. That is, normally, the missing pattern unexpectedly occurs, and therefore, also in the signal change, the signal unexpectedly decreases, and then, the signal returns to its original state after passing the missing portion.

On the other hand, normally, the width change slowly occurs or occurs in synchronization with a joint portion between exposure fields, and therefore, when such a signal change appears, the width change can be assumed. By making such a determination by the signal processing unit 321, a type of the defect may be assumed and outputted.

Also, in the inspection with including the servo pattern portion 902 on a discrete-track media substrate, as shown in FIG. 10, concentric tracks are cut on not only the discrete-track media substrate but also a hard disk substrate, and each track is divided into sectors by a radial servo pattern.

This servo pattern portion has, for example, a pattern in a lateral direction in FIG. 10 (vertical direction to the rotational direction) which is called burst pattern as shown in FIG. 10, and this is used for phase adjustment of a reference clock for reading a magnetic signal.

Such a pattern partially exists in the circumference direction. For this burst pattern, a near-field light generating pattern region is formed in the lateral direction in FIG. 10 on the near-field optical head 101, and the scattered light from this region is detected by another area S0 on the array detector 202.

Accordingly, even if the burst pattern is cut as a pattern equal to or smaller than the normal optical resolution, a signal corresponding to the burst pattern can be optically read by the near-field effect, so that the detection can be performed in the case that the servo pattern has the defect such as the missing pattern or that the phase is shifted.

Further, as shown in FIG. 11A, various patterns as different from those in a normal recording region (A) whose patterns are cut in parallel to the circumferential direction are formed on the servo pattern in addition to the burst pattern portion (B).

For example, there is a tracking pattern portion (D) in which fine dots are arranged, an address portion (C) in which a binary-digit symbol indicating a track number or a sector number is marked, or others.

With respect to the portions, the detection signals S0 to S4 are changed in accordance with the lateral-direction pattern such as the pattern corresponding to the S0 or in accordance with how the vertical-direction patterns corresponding to the S1 to the S4 are formed (as an area of an overlapping portion) in FIG. 11A.

Note that, in FIG. 11A as different from FIG. 10, a near-field light generating pattern 102' corresponding to the region S0 is not the periodic pattern but one long line-shaped pattern. Even if it is not the periodic pattern, the required change of the detection light intensity can be secured as long as a pattern length can be provided, and therefore, such a long line-shaped pattern may be provided. Alternatively, similarly to the region S0 of FIG. 10, it may be the periodic pattern.

An advantage point of using the one line pattern is that, when a pitch of a complicated and circumferential-direction pattern such as the servo pattern is different depending on cases, an obtained signal S0 can be easily predicted.

The change of this signal can be predicted as long as the arrangement of the servo pattern is known. For example, the signal S0 corresponding to the on-substrate pattern 901 of FIG. 11A is supposed to be as shown in FIG. 11B.

If the signal change pattern is different from the predicted value, the difference is outputted as the defect. That is, if an absolute value of a difference between an actual signal and a predicted signal exceeds a threshold value, the difference is outputted as the defect. Alternately, as an another method, a signal obtained from the normal inspected substrate 900 is previously stored, and, when a difference between this signal and a signal obtained by scanning the inspected substrate 900 of the inspection target is equal to or more than the threshold value, the difference is outputted as the defect.

As still another method, the defect may be detected by the comparison with a signal from an immediate-previous servo pattern because the servo pattern repeatedly appears on the circumference. However, the servo pattern for the sector number is different in each sector, and therefore, this portion is not inspected or is compared with the predicted signal or the signal obtained from the normal substrate as described above.

Alternately, this portion has the same sector number as that of a position on the circumference corresponding to a previous circumference, and therefore, only this portion is compared with a signal from the sector number portion on the previous circumference.

By such processing as described above, the pattern anomaly detection with including the servo pattern portion can be performed.

Also, when it is desired to inspect the on-substrate pattern 901 in more detail instead of slowing down the inspection speed, not the repetitive pattern but single line-shaped pattern may be used as the periodic near-field light generating pattern 102 as shown in FIG. 12.

Next, when the on-substrate pattern 901 of the inspection target is not the discrete-pattern media but a bit-patterned media in which each bit is corresponded to one dot of the pattern, while the positional shift of each track in the radial direction can be detected even in the periodic near-field light generating pattern 102 shown in FIGS. 10 to 12, the periodic near-field light generating pattern 102 as shown in FIG. 13A may be used in order to further detect a positional shift of a recording bit in the circumferential direction.

By using such a configuration, strong and weak intensities of the signals S1 to S4 are repeated in accordance with each bit. By detecting phases of these strong and weak intensities, the positional shift of the recording bit in the circumferential direction can be detected.

Also, in order to remove the strong and weak intensities of the signals corresponding to each bit, a notch filter corresponding to this frequency may be provided. As the simplest notch filter, a moving average filter for one period time corresponding to this frequency may be applied.

By using a filtered signal, the positional shift of the track in the radial direction can be detected similarly to the examples shown in FIGS. 10 to 12.

Note that, since a pitch of a dot formed in the circumferential direction on the bit-patterned media is changed in accordance with its position in the radial direction, the less dot formation in the circumferential direction inside each region corresponding to the S1 to the S4 is better.

For example, in an example shown in FIG. 13B, the dot is formed in three rows. In this case, when the dot pitch is changed by, for example, 10%, phases of both rows adjacent to a middle row are shifted by about "360°×10%=36°" from that of the middle row. However, this shift is within an allowable range. When the pitch is further changed, the periodic near-field light generating pattern 102 may be switched and used for each pitch as divided into some stages depending on a pitch size.

Alternately, when each constitution dot pattern of each of the regions the S1 to the S4 of the periodic near-field light generating pattern 102 is formed in only one row as shown in FIG. 13C, one type of the periodic near-field light generating pattern 102 may be sufficient even if the dot pitch in the circumferential direction is significantly changed.

(Fourth Embodiment)

In a fourth embodiment, the detection system 201 in the first embodiment is arranged on the same side as the near-field optical head 101 with respect to the inspected substrate 900, and the scattered light from the on-substrate pattern 901 is detected.

The configuration and the operation of the pattern inspection device for the substrate surface of the present embodiment other than the detection system 201 is the same as those of the first embodiment.

Figure 14:
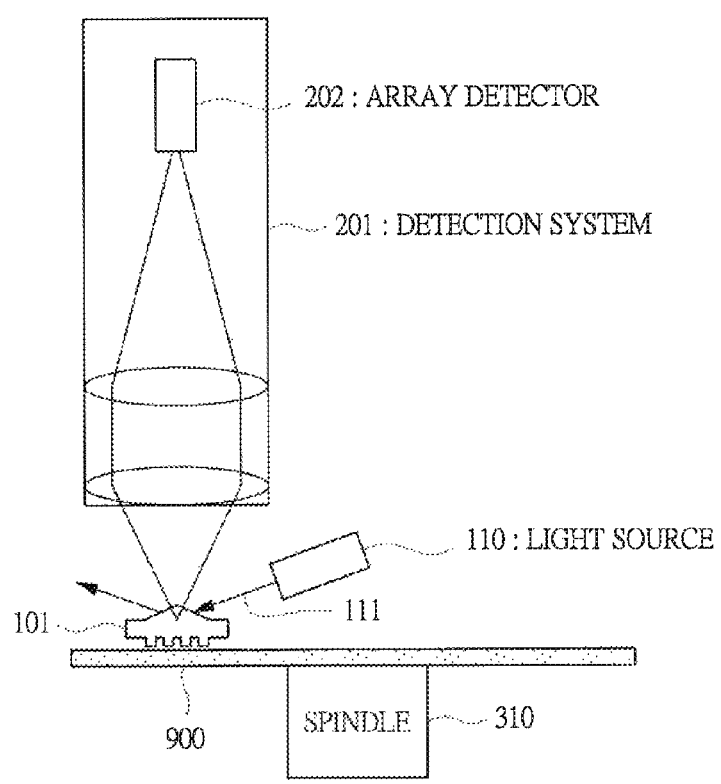
FIG. 14 is an explanatory diagram explaining an arrangement example of a detection system of a pattern inspection device for a substrate surface according to a fourth embodiment of the present invention.
Figure 15:
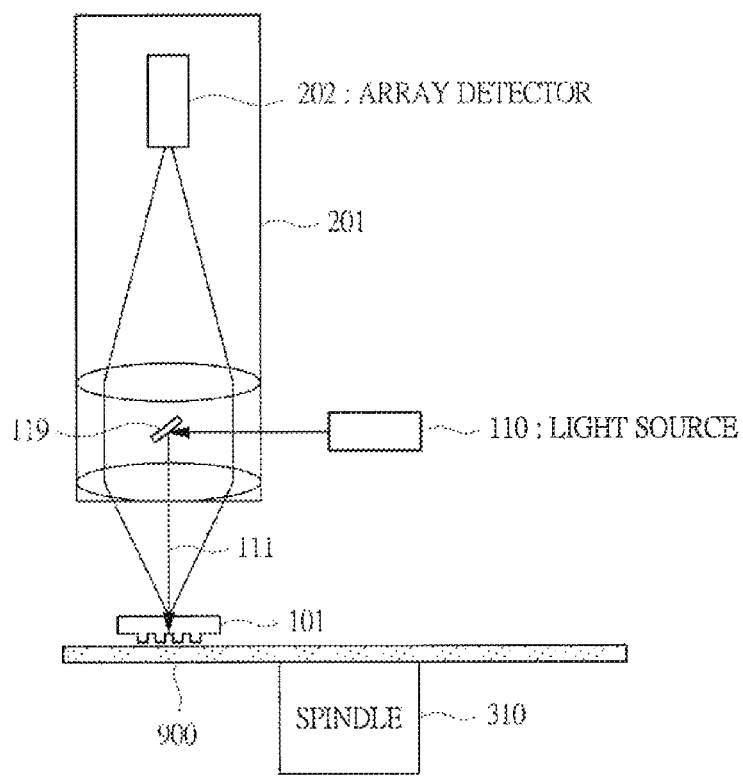
FIG. 15 is an explanatory diagram explaining another arrangement example of a detection system of a pattern inspection device for a substrate surface according to the fourth embodiment of the present invention.
Figure 16:
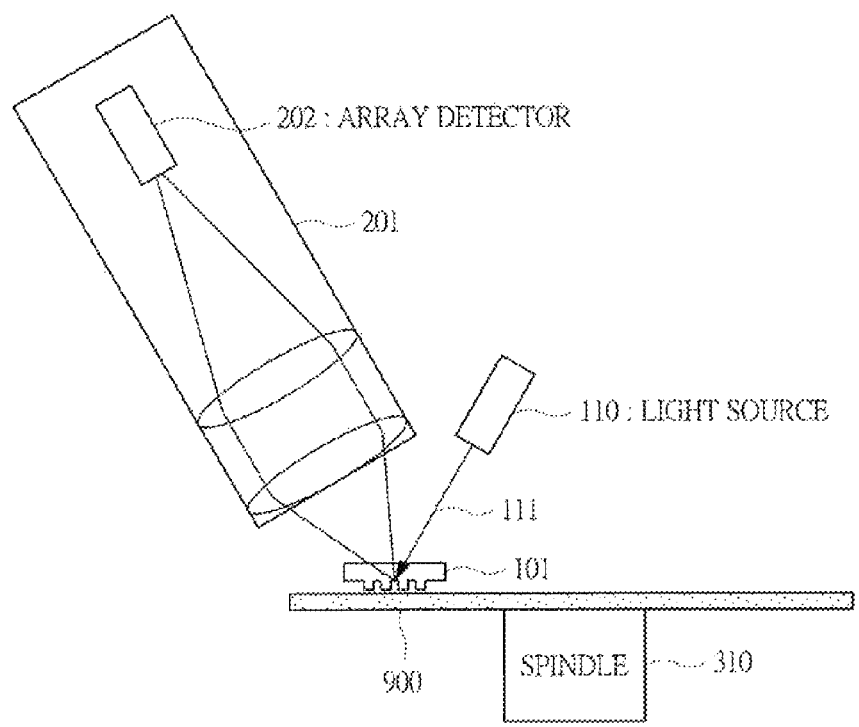
FIG. 16 is an explanatory diagram explaining still another arrangement example of a detection system of a pattern inspection device for a substrate surface according to the fourth embodiment of the present invention.

With reference to FIGS. 14 to 16, an arrangement example of the detection system of the pattern inspection device for the substrate surface according to the fourth embodiment of the present invention is described. FIGS. 14 to 16 are explanatory diagrams each explaining the arrangement example of the detection system of the pattern inspection device for the substrate surface according to the fourth embodiment of the present invention.

In the first embodiment shown in FIG. 1, the detection system 201 is arranged on an opposite side to the near-field optical head 101, and the scattered light from the on-substrate pattern 901 passes through and transmits the inspected substrate 900 and is detected.

When the inspected substrate 900 of the inspection target is made of quartz, the detection may be performed by using light having a bandwidth of 170 nm to 3.7 μm which transmits the quartz as the light source 110. For example, as a target to be desirably inspected in inspecting a recording medium, there are three types of a master substrate to be an original plate, a stamper substrate on which the master substrate is transcribed, and a recording media on which the stamper substrate is further transcribed. More particularly, the quartz is used for the stamper substrate and the master substrate often, and therefore, the above-described configuration is effective.

Although silicon is used for the master substrate sometimes, the inspection can be similarly performed with the configuration shown in FIG. 1 by using light having a bandwidth of 1.2 μm to 8 μm which transmits the silicon in this case. Since the near-field light is used, there is no limitation in a pattern size which can be inspected by the illumination wavelength, and therefore, there is an effect that there is no problem even if such a long wavelength is used.

On the other hand, when the inspection by light which does not transmit the substrate is desired, the configurations shown in FIGS. 14 to 16 are effective.

In FIG. 14, the scattered light toward the near-field optical head 101 side by the interaction between the near-field light 120 and the on-substrate pattern 901 on the inspected substrate 900 is detected by an above-positioned detection system 201. The illumination light 111 is obliquely irradiated similarly to the example shown in FIG. 1.

In FIG. 15, the illumination light 111 from the light source 110 is reflected on a mirror 119 embedded in the detection system 201, and the illumination light 111 is irradiated to the near-field optical head 101 coaxially with the detection system 201. Similarly to the example shown in FIG. 14, the scattered light toward the near-field optical head 101 side by the interaction between the near-field light 120 and the on-substrate pattern 901 on the inspected substrate 900 is detected by the above-positioned detection system 201.

In FIG. 16, the illumination light 111 is irradiated to the near-field optical head 101 obliquely from top right, and its regular reflection light is detected by a detection system 201 which is positioned obliquely upper left. Since a light absorption state of the illumination light is changed by the interaction between the near-field light 120 and the on-substrate pattern 901 on the inspected substrate 900, the same inspection can be achieved also by this change.

More particularly, it is known that the plasmon shows a strong light adsorption in a specific wavelength band by the resonance, and, by the illumination to the near-field optical head in this wavelength band, an approaching state between the periodic near-field light pattern 102 and the on-substrate pattern 901 can be sensitively detected.

(Fifth Embodiment)

In a fifth embodiment, the relative movement of the near-field optical head 101 to the inspected substrate 900 in the first embodiment is performed by another configuration.

The configuration and the operation of the pattern inspection device for the substrate surface of the present embodiment other than the configuration of the relative movement of the near-field optical head 101 to the inspected substrate 900 is the same as those of the first embodiment.

With reference to FIGS. 17 and 18, a configuration of a pattern inspection device for a substrate surface according to the fifth embodiment of the present invention is described. FIGS. 17 and 18 are configuration diagrams each showing the configuration of the pattern inspection device for the substrate surface according to the fifth embodiment of the present invention, FIG. 17 is a configuration with using an R stage, and FIG. 18 is a configuration with using an XY stage.

In an example shown in FIG. 17, an R-θ stage is achieved by mounting the spindle 310 on an R stage 312.

Also, in an example shown in FIG. 18, the relative movement is achieved by mounting the inspected substrate 900 on an XY stage 313.

Further, it is needless to say that, even when either one of an X axis and a Y axis of the XY stage 313 or both of them are configured to drive not the inspected substrate 900 side but the near-field optical head 101 and the detection system 202, the intended relative movement can be achieved.

In the foregoing, the invention made by the inventors has been concretely described based on the embodiments. However, it is needless to say that the present invention is not limited to the foregoing embodiments and various modifications and alterations can be made within the scope of the present invention.

INDUSTRIAL APPLICABILITY

The present invention relates to an inspection device for a fine pattern including a pattern which is formed on a substrate surface and whose size is equal to or smaller than an optical wavelength, and can be applied to a device or a system which inspects a pattern including a fine pattern whose size is equal to or smaller than an optical wavelength such as a patterned media disk, an integrated semiconductor, and a photonic crystal at high speed and feeds back an inspection result to a manufacturing condition.

EXPLANATION OF SYMBOLS

101 . . . near-field optical head, 102 . . . periodic near-field light generating pattern, 110 . . . light source, 111 . . . illumination light, 112 . . . magnetic plate, 113 . . . coil, 114 . . . floating surface, 115 . . . beam, 116 . . . elastic support body, 119 . . . mirror, 120 . . . near-field light, 121 . . . metal film, 122 . . . metal particles, 123 . . . metal gap, 150 . . . tracking actuator, 151 . . . space controlling actuator, 180 . . . space measuring device, 190 . . . near-field optical head moving unit, 191 . . . near-field optical head up/down system, 201 . . . detection system, 202 . . . array detector, 210 . . . detection-system moving unit, 301 . . . scattered-light inspection light source (laser), 302 . . . scattered-light detector, 303 . . . scattered-light inspection head moving unit, 310 . . . spindle, 311 . . . θ driving unit, 312 . . . R stage, 313 . . . XY stage, 320 . . . amplifier, 321 . . . signal processing unit, 330 . . . amplifier, 331 . . . signal processing unit, 340 . . . total controlling device, 341 . . . user interface, 350 . . . sample transferring mechanism, 900 . . . inspected substrate, 901 . . . on-substrate patter, 902 . . . servo pattern portion, 911 . . . floating air

The invention claimed is:

1. A pattern inspection device for a substrate surface which inspects a fine pattern on an inspection target substrate, the pattern inspection device comprising:
    a head having a fine repetitive pattern;
    a driving mechanism of scanning the inspection target substrate relatively to the head;
    a space holding mechanism of holding a space between the head and the inspection target substrate constant;
    a light irradiation mechanism of irradiating light to the head;
    a detection system of detecting an intensity of scattered light generated by interaction between the fine repetitive pattern on the head and a fine pattern on a surface of the inspection target substrate; and
    a first signal processing unit of inspecting the fine pattern on the inspection target substrate based on an output of the detection system.

2. The pattern inspection device for the substrate surface according to claim 1, wherein
    the head has at least two pattern regions having different phases from each other, and
    the detection system individually detects scattered light corresponding to each of the two pattern regions having the different phases from each other.

3. The pattern inspection device for the substrate surface according to claim 1, wherein
    the pattern on the head is formed so as to have a slightly different angle from that of an inspection target pattern on the inspection target substrate, and has a different phase from that of the inspection target pattern on the inspection target substrate in at least two regions of the pattern on the head, and
    the detection system individually detects scattered light corresponding to each of the regions of the pattern having the different phase.

4. The pattern inspection device for the substrate surface according to claim 1, wherein
    the light irradiation mechanism irradiates the light so as to satisfy a condition of total reflection.

5. The pattern inspection device for the substrate surface according to claim 1, wherein
    the pattern on the head is a pattern whose pitch is substantially equal to that of a pattern to be desirably inspected on the inspection target substrate.

6. The pattern inspection device for the substrate surface according to claim 1, wherein
the pattern on the head is a pattern whose pitch is substantially integral multiple of a pattern to be desirably inspected on the inspection target substrate.

7. The pattern inspection device for the substrate surface according to claim 4, wherein
the pattern on the head is a stripe pattern.

8. The pattern inspection device for the substrate surface according to claim 4, wherein
the pattern on the head is a pattern in which an optical near-field enhanced element is one-dimensionally or two-dimensionally arranged.

9. The pattern inspection device for the substrate surface according to claim 1, comprising:
an optical system of irradiating laser to the inspection target substrate and detecting the scattered light from the surface of the inspection target substrate; and
a second signal processing unit of detecting a foreign substance on the inspection target substrate based on an output of the optical system.

10. The pattern inspection device for the substrate surface according to claim 9, wherein,
based on a detection result of the foreign substance by the second signal processing unit, scanning of a detection position of the foreign substance on the inspection target substrate by the driving mechanism is stopped or the foreign substance is avoided by the space holding mechanism.

11. The pattern inspection device for the substrate surface according to claim 1, wherein
the light irradiated by the light irradiation mechanism is light having a bandwidth of 1.2 μm to 8 μm which transmits a silicon substrate.

12. The pattern inspection device for the substrate surface according to claim 1, wherein
the light irradiated by the light irradiation mechanism is light having a bandwidth of 170 nm to 3.7 μm which transmits a quartz substrate.

13. A pattern inspection method of a pattern inspection device for a substrate surface, which inspects a fine pattern on an inspection target substrate, the pattern inspection method comprising the steps of:
scanning the inspection target substrate relatively to a head having a fine repetitive pattern by a total controlling device of totally controlling the pattern inspection device;
holding a space between the head and the inspection target substrate constant;
irradiating light to the head;
detecting an intensity of scattered light generated by interaction between the fine repetitive pattern on the head and a fine pattern on a surface of the inspection target substrate; and
based on a detection result, inspecting the fine pattern on the inspection target substrate.

\* \* \* \* \*